(12) United States Patent
Jorgenson et al.

(10) Patent No.: US 7,233,825 B2
(45) Date of Patent: Jun. 19, 2007

(54) IMPEDANCE MEASUREMENT IN IMPLANTED DEVICE

(75) Inventors: David J. Jorgenson, Bloomington, MN (US); Christopher M. Manrodt, White Bear Lake, MN (US); Robert M. Ecker, Lino Lakes, MN (US); Lawrence C. McClure, Forest Lake, MN (US); Charles H. Malmskog, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 765 days.

(21) Appl. No.: 10/367,299

(22) Filed: Feb. 15, 2003

(65) Prior Publication Data

US 2004/0162591 A1    Aug. 19, 2004

(51) Int. Cl.
*A61N 1/36* (2006.01)
(52) U.S. Cl. ............................. 607/28; 607/27; 607/62
(58) Field of Classification Search .................... 607/9, 607/27–28, 62–63; 600/547; 128/901
See application file for complete search history.

(56) References Cited

U.S. PATENT DOCUMENTS

| | | | |
|---|---|---|---|
| 4,091,818 A | 5/1978 | Brownlee et al. | |
| 4,549,548 A | 10/1985 | Boute et al. | |
| 4,606,349 A | 8/1986 | Livingston et al. | |
| 5,003,975 A * | 4/1991 | Hafelfinger et al. | 607/28 |
| 5,534,018 A | 7/1996 | Wahlstrand et al. | |
| 5,978,710 A | 11/1999 | Prutchi et al. | |
| 6,493,586 B1 * | 12/2002 | Stahmann et al. | 607/27 |
| 6,901,292 B2 * | 5/2005 | Hrdlicka et al. | 607/27 |

FOREIGN PATENT DOCUMENTS

| | | |
|---|---|---|
| EP | 0 338 363 | 1/1989 |
| WO | WO 01/80940 | 11/2001 |

* cited by examiner

*Primary Examiner*—Robert E. Pezzuto
*Assistant Examiner*—Jessica L. Reidel
(74) *Attorney, Agent, or Firm*—Paul H. McDowall; Girma Wolde-Michael

(57) ABSTRACT

In an implantable medical device having an electrical lead coupled to tissue of a user and a circuit for measuring the impedance of the lead, a method and apparatus for responding to impedance variations in the lead which includes measuring the impedance of the lead while monitoring physiologic parameters of the user, detecting the presence or absence of electromagnetic interference, and if the impedance of the lead is out-of-range, determining whether the electromagnetic interference exceeds a predetermined value, and if the electromagnetic interference exceeds a predetermined value, administering a therapy to the tissue of the user.

12 Claims, 3 Drawing Sheets

IMPEDANCE MEASUREMENT IN IMPLANTED DEVICE

FIELD OF THE INVENTION

The present invention generally relates to impedance measuring, and more particularly relates to impedance measuring in an implantable medical device, especially in the presence of electromagnetic interference.

BACKGROUND OF THE INVENTION

Implantable medical devices (IMDs) have many functions including the delivery of therapies to cardiac patients, neuro-stimulators, muscular stimulators, and others. For purposes of this application reference will be made only to implantable cardiac devices, it being understood that the principles herein may have applicability to other implantable medical devices as well.

An implantable cardiac device (ICD) may be a device commonly referred to as a pacemaker, which is used to stimulate the heart into a contraction if the sinus node of the heart is not properly timing, or pacing, the contractions of the heart. Modern cardiac devices also perform many other functions beyond that of pacing. For example, some cardiac devices may also perform therapies such as defibrillation and cardioversion as well as providing several different pacing therapies, depending upon the needs of the user and the physiologic condition of the user's heart. For convenience, all types of implantable cardiac devices will be referred to herein as ICDs, it being understood that the term, unless otherwise indicated, is inclusive of an implantable device capable of administering any of a number of therapies to the heart of the user.

In typical use, an ICD is implanted in a convenient location usually under the skin of the user and in the vicinity of the one or more major arteries or veins. One or more electrical leads connected to the pacemaker are inserted into or on the heart of the user, usually through a convenient vein or artery. The ends of the leads are placed in contact with the walls or surface of one or more chambers of the heart, depending upon the particular therapies deemed appropriate for the user.

One or more of the leads is adapted to carry a current from the pacemaker to the heart tissue to stimulate the heart in one of several ways, again depending upon the particular therapy being delivered. The leads are simultaneously used for sensing the physiologic signals provided by the heart to determine when to deliver a therapeutic pulse to the heart, and the nature of the pulse, e.g., a pacing pulse or a defibrillation shock.

The sensing of the physiologic signal from the heart requires a very sensitive sensing method since the signals sensed are of quite low amplitude. The presence of external, or non-physiologic, electromagnetic interference (EMI), if the field is large enough, can compromise the cardiac sensing function such that the pacemaker may fail to deliver a needed therapy or may deliver an unwanted therapy. Some types of non-physiologic EMI, such as continuous wave at high frequencies, can easily be distinguished from physiologic signals and can thus be ignored or rejected by the pacemaker circuitry. Other forms of non-physiologic EMI, however, are not easily distinguishable from physiologic signals and therefore can block or override the desired physiologic signals.

Many state-of-the-art ICDs are capable of performing either bipolar or unipolar sensing and pacing in either chamber of the heart. Unipolar pacing requires an elongated lead having only one insulated conductor therein and only one generally distal electrode disposed thereon. In most unipolar configurations the protective canister of the ICD is conductive and functions as an electrode in pacing or sensing. For bipolar pacing and/or sensing a lead having two mutually insulated conductors disposed thereon is required. Typically, one electrode is disposed at the distal end of the lead and is referred to as the "tip" electrode, while the second electrode is spaced somewhat back from the distal end of the lead and is referred to as the "ring" electrode. The current path for bipolar pacing extends from the pulse generator in the ICD, along a first of the two lead conductors to the tip electrode, through the cardiac tissue to the ring electrode and back to the ICD along the second of the two conductors.

Most modern ICDs may be programmed to pace and sense in either the bipolar or unipolar mode. This gives the implanting physician considerable flexibility in configuring an ICD system to suit the particular needs of a given patient or user. Additionally, if one of the two leads in a bipolar ICD were to fail for some reason, (e.g., breakage of a conductor due to metal fatigue, an open outer coil, an ineffective ring set screw connection, poor connections, tissue degradation at the electrode site, oxidation, etc.) it would be necessary to reprogram the ICD into unipolar pacing and sensing mode in order for the ICD to continue to perform properly.

In order to detect the failure of a lead in a bipolar ICD unit the impedance of the leads is monitored continuously and, in the event an impedance is detected that is outside a specified range, the ICD is automatically switched to unipolar pacing and sensing until the problem can be rectified. The switch can take several tens of seconds, however, because the impedance measurement must be confirmed by a series of readings before the switch is made. During this time, no pulses are provided, which results in less than optimal therapy. The delay is necessary because a high impedance reading may be caused by electromagnetic interference (EMI). In such cases an out-of-range impedance may be detected when no lead failure has occurred.

Accordingly, it is desirable provide a mechanism and method such that therapy can continue in the event of an out-of-range impedance measurement Other desirable features and characteristics of the present invention will become apparent from the subsequent detailed description of the invention and the appended claims, taken in conjunction with the accompanying drawings and this background of the invention.

BRIEF SUMMARY OF THE INVENTION

In an implantable medical device having an electrical lead coupled to tissue of a user and a circuit for measuring the impedance of the lead, a method for responding to impedance variations in the lead which includes measuring the impedance of the lead while monitoring physiologic parameters of the user, detecting the presence or absence of electromagnetic interference, and if the impedance of the lead exceeds a predetermined value, determining whether the electromagnetic interference exceeds a predetermined value, and if the electromagnetic interference exceeds a predetermined value, administering a therapy to the tissue of the user.

Also provided is, in an implantable cardiac device having a pulse generator for normally producing bipolar pulses that is capable of switching to producing unipolar pacing pulses, a bipolar electrical lead coupling the device to a heart, means for measuring the impedance of the bipolar lead while producing bipolar pacing pulses, and a detector for detecting the presence or absence of electromagnetic interference, whereby, if the impedance of the bipolar lead exceeds a predetermined value, the pulse generator produces the next pulse as a unipolar pacing pulse and if electromagnetic interference is present the pulse generator returns to production of bipolar pacing pulses.

BRIEF DESCRIPTION OF THE DRAWINGS

The present invention will hereinafter be described in conjunction with the following drawing figures, wherein like numerals denote like elements.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

Figure 1:
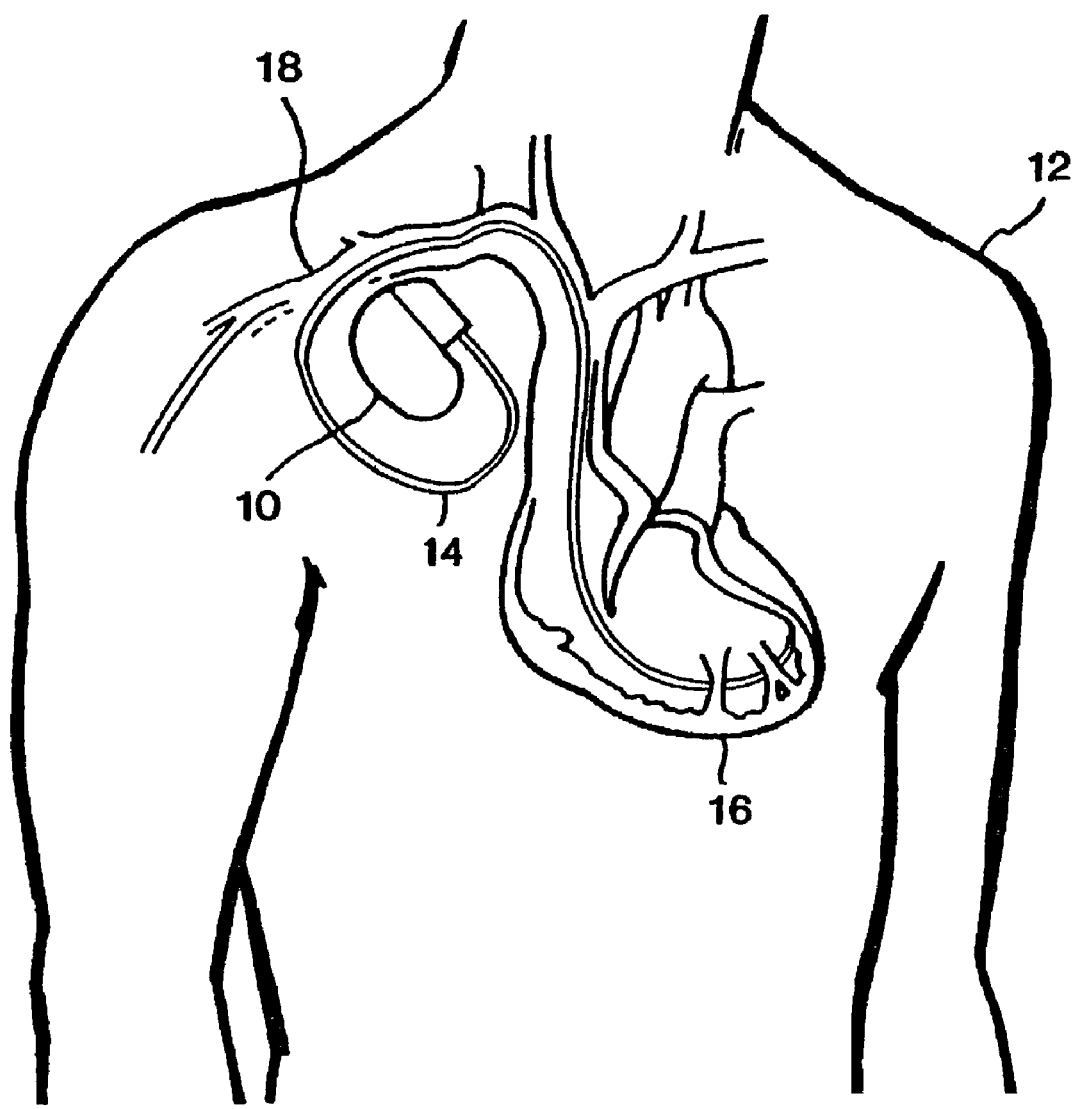
FIG. 1 is an illustration of an implantable cardiac device having been implanted in a conventional manner in a patient.

FIG. 1 is an illustration showing generally where a implantable cardiac device (ICD) 10 is placed in a conventional manner in a patient 12. ICD 10 is conventionally housed within a hermetically sealed, biologically inert outer canister, which itself may be of a conductive material and serve as an electrode in the ICDs pacing/sensing circuit. One or more leads, collectively identified as 14 are electrically coupled to ICD 10 in a conventional manner, extending into the patient's heart 16 via a vein 18. Disposed generally near the distal end of lead 14 are one or more exposed conductive electrodes for receiving electrical cardiac signals and/or for delivering electrical stimuli or other therapies to heart 16. Lead 14 may be implanted with its distal end in either the atrium or the ventricle of heart 16. Lead 14 is preferably a bipolar lead such that lead 14 actually has two separate and mutually insulated leads, the first having a terminal at the distal end of lead 14 and the second having a terminal near, but set back from the distal end. Such leads are well known in the art.

An implantable cardiac device may have a pulse generator for normally producing bipolar pulses that is capable of switching to producing unipolar pacing pulses. A bipolar electrical lead couples the device to a heart. There are provided means for measuring the impedance of the bipolar lead while producing bipolar pacing pulses, whereby, if the ICD is programmed to pace or sense in a bipolar configuration, and the impedance of the bipolar lead is out of a normal, predetermined, range, the pulse generator provides unipolar pacing pulses. When the bipolar impedance returns to within a predetermined value, the pulse generator will return to bipolar pacing pulses.

Figure 2:
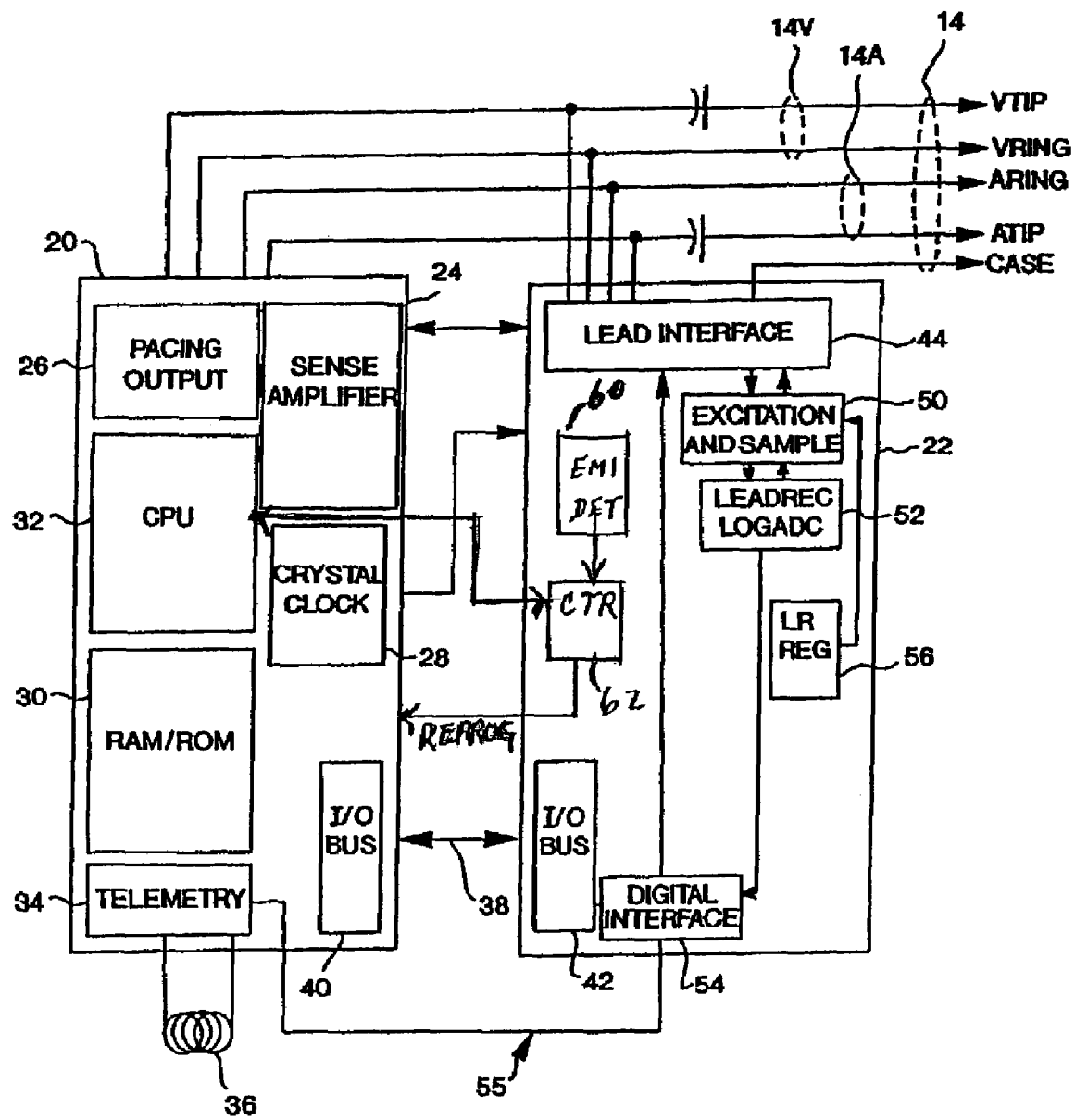
FIG. 2 is a block diagram of an implantable cardiac device usable in the instant invention.

FIG. 2 is a block diagram of an implantable cardiac device 10 usable in the instant invention. While the device of FIG. 2 is shown as a pacemaker, it is understood that other ICDs or IMDs could also be used, including devices such as defibrillators, cardioversion devices, neuro-stimulators, and the like. ICD 10 comprises a primary pacing/control circuit 20 and a lead recognition circuit 22. Of course lead recognition circuit 22 may be associated with other circuitry for performing other cardiac functions such as minute ventilation sensing. Much of the circuitry associated with pacing control circuit 20 may be of conventional design in accordance with U.S. Pat. No. 5,534,018, assigned to the assignee of the instant invention, and which is incorporated by reference herein in its entirety, including those documents incorporated into that patent by reference.

To the extent that certain components of ICD 10 are conventional, they will not be described in great detail here, since it is believed that the design and implementation of such components would be a matter of routine to those of ordinary skill in the art. For example, pacing/control circuit 20 includes a sense amplifier circuit 24, pacing output circuit 26, a crystal clock 28, a random-access memory and read only memory (RAM/ROM) unit 30, a central processing unit (CPU) 32 and a telemetry circuit 34, all of which are well known in the art.

ICD 10 preferably includes an internal telemetry circuit 34 so that it is capable of being programmed or reprogrammed externally. Programmers and telemetry circuit are well known in the art. Coil 36 is a pick-up coil or antenna that allows communication between the telemetry circuit 34 and the external programmer (not shown).

ICD 10 is coupled to leads 14 which, when implanted, extend transvenously between the implant site of ICD 10 and the patient's heart. For clarity, the connection between leads 14 and the various components of ICD 10 are not shown in FIG. 2 although it will be apparent to those of ordinary skill in the art that, for example, leads 14 will necessarily be coupled, either directly or indirectly to sense amplifier 24 and pacing output circuit 26, in accordance with common practice, such that cardiac electric signals may be conveyed to sensing circuitry 24 and pacing pulses may be delivered to cardiac tissue, via leads 14.

In the present embodiment two bipolar leads are employed, an atrial lead 14A having atrial tip and ring electrodes (ATIP and ARING), and a ventricular lead 14V having ventricular tip and ring electrodes (VTIP and VRING). Those of ordinary skill in the art will appreciate that a separate, electrically insulated conductor extending along the length of leads 14A and 14V is associated with each of the electrodes ATIP, ARING, VTIP, and VRING. That is, electrical signals applied, for example to the VRING electrode are conducted along lead 14V on a first conductor, whereas signals applied to the VTIP electrode are conducted along a second, separate conductor in lead 14V. In addition, as noted above, the conductive, hermetically sealed canister of ICD 10 serves as an indifferent electrode (CASE in FIG. 2).

As previously noted, central processing unit 32 may be an off-the-shelf microprocessor or microcontroller. Although specific connections between CPU 32 and the other components of ICD 20 are not shown in FIG. 2, it will be apparent to those skilled in the art that CPU 32 functions to control the timed operations of pacing output circuit 26 and sense amplifier circuit 24 under control of programming stored in RAM/ROM 30. Crystal oscillator circuit 28 provides the main timing clock signals to pace/control circuit 20 and to lead recognition circuit 22.

It is also understood that the circuitry of ICD 10 is powered by a battery inside the hermetically sealed case of ICD 10 in accordance with common practice in the art. For the sake of clarity, the battery and the connections between the battery and the various circuit elements are not shown.

Pacing output circuit 26, which functions to generate pacing stimuli under control of signals issued by CPU 32, may be, for example, of the type disclosed in U.S. Pat. No. 4,476,868 to Thompson, entitled "Body Stimulator Output Circuit," which patent is hereby incorporated herein by reference in its entirety. Again, however, it is believed that those of ordinary skill in the art could select from among many various types of prior art pacing output circuits which would be suitable for the purposes of practicing the present invention.

As shown in FIG. 2, pace/control circuit 20 is coupled to lead recognition circuit 22 by means of multiple signal lines, designated collectively as 38 in FIG. 2. An I/O interface 40 in pace/control circuit 20 and a corresponding I/O interface 42 in lead recognition circuit 22 functions to coordinate the transmission of signals between the two units 20 and 22.

With continued reference to FIG. 2, lead recognition circuit 22 includes a lead interface circuit 44, which essentially functions as a multiplexer to selectively couple the lead conductors associated with the ATIP, ARING, VTIP, and VRING electrodes of leads 14A and 14V to the remaining components of lead recognition circuitry 22. In the preferred embodiment, the selection of particular conductors can be accomplished by interface circuit 44 under control of control signals originating from pace/control circuit 20 and communicated to lead interface circuit 44 via lines 38.

Coupled to lead interface circuit 44 in lead recognition circuit 22 is an excitation and sample circuit 50 which functions to generate biphasic excitation pulses which are conveyed along leads 14A and 14V for the purposes of measuring impedance between various combinations of electrodes ATIP, ARING, VTIP, and VRING, as determined by the multiplexing function of lead interface circuit 44. In addition, excitation and sample circuit 50 performs a sampling function on electrical signals present on the conductors of leads 14A and 14V. As noted above, the hermetically sealed case of ICD 10 may be used as well.

This is accomplished through delivery of sub-threshold biphasic voltage pulses on the possible pacing/sensing paths (atrial unipolar and bipolar, ventricular unipolar and bipolar, and the case), such that the impedances observed along those paths can be evaluated.

To this end, excitation and sample circuit 50 includes circuitry for generating the small sub-threshold biphasic voltage pulses, which, through lead interface circuit 44 are periodically and sequentially issued along each of the possible pacing paths. By sub-threshold is meant that the voltage pulses are well below the level of voltage and duration that would be applied by a pacing pulse.

The sample values obtained by excitation and sample circuit 50 are provided to a logarithmic analog-to-digital converter ("logadc") circuit 52. As its name suggests, logadc circuit 52 performs a logarithmic analog-to-digital conversion function on the sample values obtained by sample and excitation circuit 50, resulting in the derivation of values corresponding to the current and voltage on the conductors of leads 14A and 14V and the case. These values, in turn, are used to derive an impedance value reflecting the impedance associated with a given pacing path defined by the conductors of leads 14A and 14V. This impedance value is determined in a digital interface circuit 54 which also functions to coordinate the transfer of digital information between lead recognition circuit 22 and pace/control circuit 20 on lines 38.

Finally, a lead recognition voltage regulator ("Irreg") circuit 56 is provided to define a reference voltage used by excitation and sample circuit 50.

The impedance values obtained are provided to the CPU 32 for comparison with other received impedance values and for comparison with impedance values that represent impedances within the acceptable range for bipolar pacing/sensing.

In prior art ICDs, the receipt of an out-of-range impedance value would cause the ICD to continue to deliver pacing pulses even if they were ineffective due to the high impedance for a period of time, sometimes several tens of seconds, to determine whether the impedance value is correct or is the result of an anomaly such as the presence of an EMI field in the vicinity of the ICD that may have caused the out-of-range impedance measurement. Subsequently, the ICD will either resume bipolar pacing or switch to unipolar pacing in which only one of the conductive pathways is necessary to provide a pacing pulse, the other terminal being provided by the canister of the ICD. During this time, the patient may not receive optimal therapy. The instant invention overcomes this situation by providing an alternative solution.

Lead recognition circuit 22 has associated therewith an EMI detector 60 that is coupled to a counter 62. The EMI detector 60 is capable of detecting the presence of electromagnetic interference above a predetermined threshold level that may be disruptive to the operation of the ICD. The counter 62 is coupled to the CPU 32 to receive signals indicating that the impedance measurement for the lead delivering pacing pulses is out-of-range. The counter is incremented upon receipt of an indication that the impedance of a lead is out-of-range and that a unipolar pulse has been issued, and after a predetermined number of counts, the counter causes the ICD 20 to be reprogrammed to a unipolar pacing/sensing mode.

Figure 3:
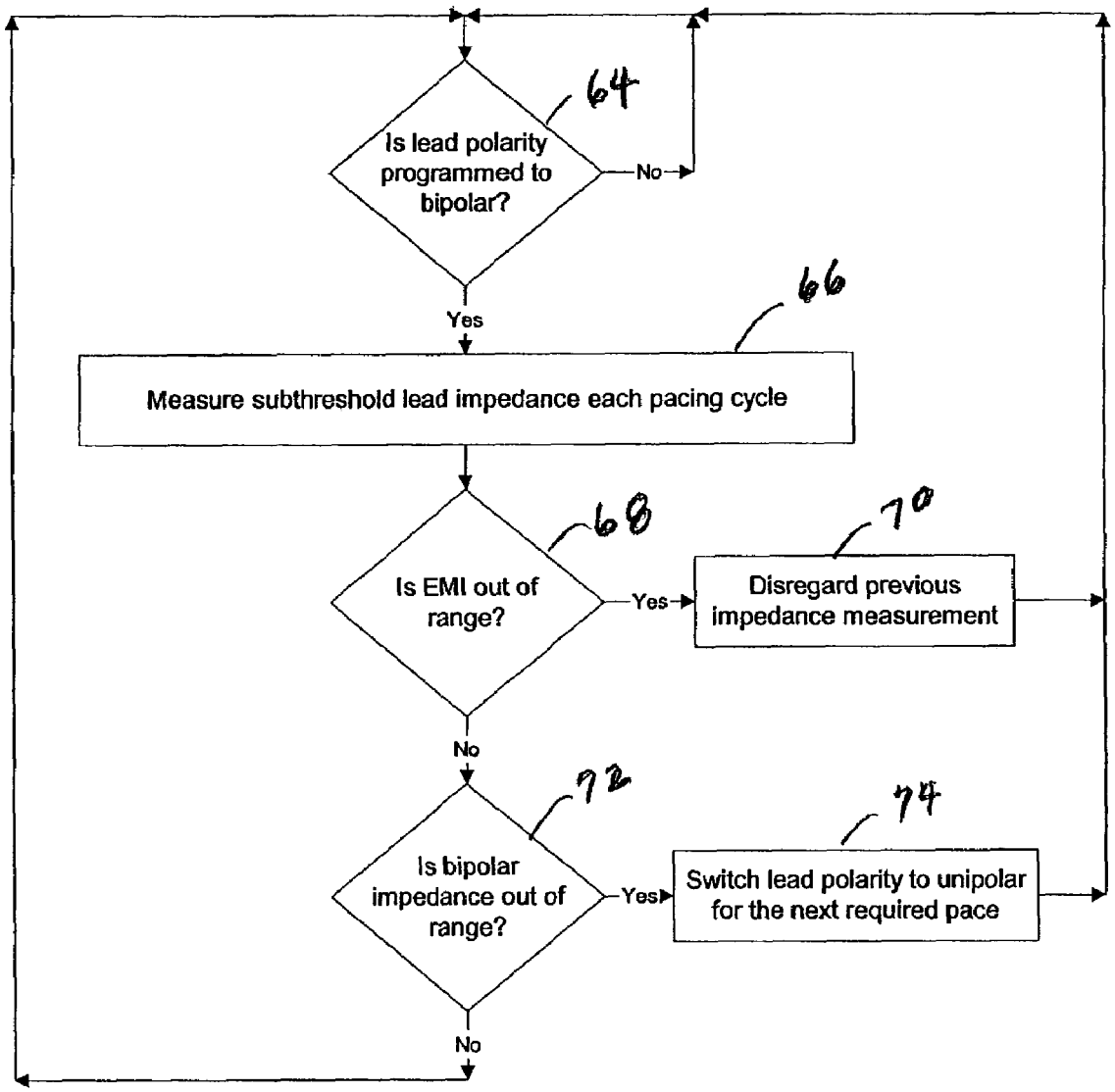
FIG. 3 is a flow chart describing the operation of the implantable cardiac device of the instant invention.

FIG. 3 is a flow chart describing the operation of the implantable cardiac device of the instant invention. A determination is first made as to whether the lead polarity is programmed in a bipolar pace/sense mode 64. If so, the sub-threshold lead impedance is sensed with each pacing cycle 66, and a determination is made as to whether the EMI sensed is out-of-range 68. If the EMI is out-of-range, that is, an EMI signal is detected, the impedance measurement is ignored 70 and normal bipolar pacing/sensing continues. If the EMI is not out-of-range, the bipolar impedance is checked 72. If the impedance is out-of-range, the polarity of the next pacing pulse is switched to unipolar, so that the patient does not miss a scheduled therapy. The process is repeated with each successive pacing/sensing cycle.

In order to make a final determination that there is a problem with lead impedance rather than merely an EMI problem, a counter 62 (FIG. 2) is provided. Counter 62 is incremented each time a unipolar pacing pulse is detected. Since unipolar pulses are inhibited (70 in FIG. 3) if the EMI level is out-of-range, unipolar pulses are counted only when the EMI is in normal range. After a predetermined number of unipolar pulses are provided over a predetermined period, i.e., the counter could be reset by known means to zero if a series of good measurements occurred over a period of time, an assumption is made that the lead is indeed faulty, and the counter 62 issues a signal to the CPU 32 to reprogram the ICD to unipolar mode.

By this mechanism the patient continues to receive pacing pulses even though the impedance measurement is initially out-of-range, and will receive pacing pulses until the problem may be resolved with lead replacement or by some other means.

Impedance measurements may be used for a number of other diagnostic or therapeutic tasks. For example, impedance measurement can be used to determine minute ventilation in order to adjust the pacing rate of an ICD in those instances when the user is engaged in strenuous activities which require a higher heart rate than normal, or simply to confirm the polarity programming of the ICD. The use of an EMI measurement in conjunction with any of a number of impedance measurement diagnostics can ensure that the impedance measurements are not unduly affected by the presence of disruptive EMI.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. In an implantable cardiac device having a pulse generator for producing bipolar or unipolar pacing pulses and a bipolar electrical lead coupling the device to a heart, a method for responding to out-of-range impedance in the lead comprising:

measuring the impedance of the bipolar lead while producing bipolar pacing pulses;

detecting the presence or absence of electromagnetic interference;

if the impedance of the bipolar lead is out-of-range, producing the next pulse as a unipolar pacing pulse; and if electromagnetic interference is present, returning to production of bipolar pacing pulses.

2. A method as set forth in claim 1 wherein:

upon determining that the impedance exceeds the certain value, a count is made of the number of unipolar pacing pulses produced, and when the number of unipolar pulses produced reaches a predetermined number, the cardiac device is switched permanently into producing unipolar pacing pulses.

3. A method as set forth in claim 2 wherein the count of the number of unipolar pacing pulses is made over a predetermined period of time.

4. A method as set forth in claim 2 wherein, if electromagnetic interference is detected, a count of the following unipolar pulse is not made.

5. In an implantable medical device having an electrical lead coupled to tissue of a user and a circuit for measuring the impedance of the lead, a method for responding to impedance variations in the lead comprising:

measuring the impedance of the lead while monitoring physiologic parameters of the user;

detecting the presence or absence of electromagnetic interference;

if the impedance of the lead is out-of-range, determining whether the electromagnetic interference exceeds a predetermined value; and if the electromagnetic interference exceeds a predetermined value, administering a therapy to the tissue of the user.

6. A method as set forth in claim 5 wherein:

if the electromagnetic interference does not exceed the predetermined value an alternate therapy is administered to the tissue of the user.

7. An implantable cardiac device comprising:

a pulse generator for normally producing bipolar pulses that is capable, of switching to producing unipolar pacing pulses;

a bipolar electrical lead coupling the device to a heart;

an excitation and sample circuit for measuring the impedance of the bipolar lead during the production of bipolar pacing pulses; and a detector for detecting the presence or absence of electromagnetic interference;

whereby, if the impedance of the bipolar lead is outside a predetermined value, the pulse generator produces the next pulse as a unipolar pacing pulse and if electromagnetic interference is present the pulse generator returns to production of bipolar pacing pulses.

8. An implantable cardiac device as set forth in claim 7 further comprising a counter coupled to the pulse generator and wherein:

the counter is incremented by a count for each unipolar pacing pulses produced, and when the number of unipolar pulses produced reaches a predetermined number, the cardiac device is switched permanently into producing unipolar pacing pulses.

9. An implantable cardiac device as set forth in claim 8 wherein the counter is incremented by a count for each unipolar pulse produced over a predetermined period of time.

10. An implantable cardiac device as set forth in claim 8 wherein, if electromagnetic interference is detected, the counter is not incremented on the following unipolar pulse.

11. An implantable cardiac device as set forth in claim 7 wherein a first electrode for carrying unipolar pulses is the bipolar lead.

12. An implantable cardiac device as set forth in claim 7 wherein a second electrode for carrying unipolar pulses is the cardiac device case.

* * * * *